United States Patent [19]

Rubio et al.

[11] Patent Number: 5,780,250
[45] Date of Patent: Jul. 14, 1998

[54] IMMUNOASSAY STANDARDS FOR POLYAROMATIC HYDROCARBON DETECTION

[75] Inventors: Fernando M. Rubio, Doylestown, Pa.; Timothy S. Lawruk, New Castle, Del.; Charles E. Lachman, Levittown, Pa.

[73] Assignee: Strategic Diagnostics, Inc., Newark, Del.

[21] Appl. No.: 606,284

[22] Filed: Feb. 23, 1996

[51] Int. Cl.$^6$ ................................................. G01N 33/553
[52] U.S. Cl. .................... 435/7.93; 435/967; 436/526; 436/815
[58] Field of Search .................. 435/7.93, 967; 436/526, 815

[56] References Cited

U.S. PATENT DOCUMENTS 5,449,611  9/1995  Friedman et al. ............... 435/7.93

OTHER PUBLICATIONS

Meisenecker, K. et al., Analytical Methods and Instrumentation, vol. 1, No. 2, pp. 114–118 (1993).
Roda, A. et al., Environmental Technology, vol. 12, pp. 1027–1035 (1991).
Roda, A. et al., Analytica Chimica Acta, vol. 298, pp. 53–64 (1994).
Scheepers, P.T.J. et al., Fresenius J. Anal. Chem., vol. 351, pp. 660–669 (1995).
Scheepers, P.T.J. et al., Toxicology Letters, vol. 72, pp. 191–198 (1994).
Marco, M.–P. et al., J. Org. Chem., vol. 58, pp. 7548–7556 (1993).
Marco, M.–P. et al., Chem. Res. Toxicol., vol. 6, pp. 284–293 (1993).
Harper, N. et al., Organohalogen Compd., vol. 13, (1993), Dioxin '93, 13th International Symposium on Chlorinated Dioxins & Related Compounds.
McDonald, P.P., et al., Journal of AOAC International, vol. 77, pp. 466–472 (1994).
Knopp, D. et al., Egypt. J. Anal. Chem. vol. 3, pp. 108–112 (1994).
Mapes, J. P. et al., Hydrocarbon Contaminated Soils and Groundwater, vol. 3, pp. 47–56 (1993).
Kado, N.Y. and Wei, E.T., J. Nat'l Cancer Inst., vol. 61, No. 1, pp. 221–225 (1978).
Allen et al., in Contam. Soils, pp. 37–46 (1992) Kostecki, P.T. et al., (editors), published by Lewis, Boca Raton, Florida.
Kramer, P. et al., J. Chem. Agric. Food Chem., vol. 42, pp. 934–943 (1994).

*Primary Examiner*—Mary E. Ceperley
*Attorney, Agent, or Firm*—Volpe & Koenig, P.C.

[57] ABSTRACT

An immunoassay directed at certain analytes that are polyaromatic hydrocarbons, such that the immunoreactive standard used for assay calibration allows the creation of calibration solutions of superior stability.

11 Claims, 6 Drawing Sheets

FIG. 6

IMMUNOASSAY STANDARDS FOR POLYAROMATIC HYDROCARBON DETECTION

FIELD OF THE INVENTION

The invention relates to improvements in immunoassays for polycyclic aromatic hydrocarbons analytes.

BACKGROUND

Polycyclic aromatic hydrocarbons (PAHs) are a group of compounds composed of two or more fused rings. The U.S. Environmental Protection Agency has identified 16 unsubstituted PAHs, each containing from two to six fused rings, as priority pollutants: naphthalene, acenaphthalene, phenanthrene, anthracene, fluorene, acenaphthylene, benzo|a|anthracene, pyrene, fluoranthene, chrysene, benzo|b| fluoranthene, benzo|k|fluoranthene, benzo|a|pyrene, dibenzo|a,h|anthracene, indeno|1,2,3-cd|pyrene and benzo |g,h,i|perylene.

A rapidly growing technology for measuring contamination by such compounds in water and other substances is the immunoassay, an assay wherein antibodies with high specificity for particular PAHs play a key role. Nevertheless, the standards used to calibrate such immunoassays frequently are a problem because of their deterioration with time of storage. Such instability affects the value of commercial immunoassay kits, wherein a period of months can elapse between the time the standard solutions are made by the manufacturer and the time the standard solutions are actually used.

S. B. Friedman et al., U.S. Pat. No. 5,449,611, identified phenanthrene as a useful standard in an immunoassay directed at phenanthrene and certain other PAHs, anthracene, fluorene, benzo(a)anthracene, chrysene, and fluoranthene. Those other PAHs were also identified as potential standards.

K. Meisenecker et al., *Analytical Methods and Instrumentation*, vol. 2, pp. 114–118 (1993), identified 4-(1-pyrenyl)butyric acid as a useful standard in an immunoassay directed at pyrene and certain other PAHs.

A. Roda et al., (*Environmental Technology*, Vol. 12, pp. 1027–1035 (1991) and Analytica Chimica Acta Vol. 298, pp. 53–64 (1994)) used benzo(a)pyrene in an immunoassay directed at unknown amounts of benzo(a)pyrene and certain other PAH's in tap water, river water, and other water sources.

P. T. J. Scheepers et al. (*Fresnius J. Anal. Chem.*, vol. 351 pp 660–669 (1995) and *Toxicology Letters*, vol. 72, pp. 191–198 (1994)) used 1-aminopyrene in an immunoassay directed at unknown amounts of 1-aminopyrene and certain other PAHs in urine samples.

M.-P. Marco et al., (*J. Org. Chem.*, vol. 58, pp. 7548–7556 (1993) and *Chem. Res. Toxicol.*, vol. 6, pp. 284–293 (1993)) identified NaphMA ((N-acetyl-S-(1,2-dihydro-1-hydroxy-2-naphthyl)cysteine) and (N-acetyl-S-(1,2-dihydro-2-hydroxy-2-naphthyl)cysteine)), which are mercapturic acid conjugates of naphthalene as useful standards in an immunoassay for NaphMA and certain other PAHs in urine samples.

N. Y. Kado and E. T. Wei (*J. Natl. Cancer Inst.*, vol. 61, pp. 221–225) identified benzo(alpha)pyrene as a useful standard in an immunoassay for benzo(alpha)pyrene.

BRIEF SUMMARY OF THE INVENTION

The present invention is an immunoassay directed at polyaromatic hydrocarbons wherein the improvement in the immunoassay is the use of certain compounds as standards that are not only reactive in the immunoassay but also can be used to create assay calibration solutions of superior stability.

DESCRIPTION OF THE INVENTION

In a general aspect, the invention is an immunoassay for an analyte (which analyte may be one of several analytes being tested for in the immunoassay), said immunoassay a process that comprises the steps of:

1) reacting a sample with an antibody preparation, said sample comprising an unknown amount of analyte, said antibody reactive against said analyte, 2) reacting a known amount of standard with an antibody preparation of the same specificity as that used in step (1), it being required that the standard is a compound that is immunoreactive with the antibody preparation,

3) calculating the amount or an upper or lower limit to the amount of analyte present in the sample used in step (1), wherein the analyte is a compound that comprises at least two fused benzene rings, (and, if the analyte consists of rings in addition to the two fused benzene rings, then preferably there are not more than six rings, and each of the additional rings is either a six atom-ring, such as benzene, or a five atom-ring such as cyclopentane, the atoms of the additional rings being selected from carbon, oxygen, nitrogen, and sulfur), wherein a benzene ring in the analyte may be substituted at one or more of its six carbon atoms, wherein any substituent on said benzene ring that is not I, Cl, Br, OH, —CH$_3$, or —NO$_2$, has a backbone chain that does not have more than six atoms, wherein either the standard is a compound with the structure wherein $R_1$, $R_2$, $R_3$, $R_4$, $R_5$, $R_6$, $R_7$, $R_8$, $R_9$, and $R_{10}$, are substituents, wherein one or two of said substituents are not H (i.e., not hydrogen) and the other substituents are H, and a substituent that is not H is either OH, COH (i.e., carboxaldehyde), $CH_2OH$, $CH_2(CH_2)_xOH$, $CO_2H$, $NH_2$, CN, $SO_3H$, $NO_2$, or wherein the leftmost carbon is the point of attachment to the phenanthrene moiety (a substituent that is not H is preferably either OH, COH, $CH_2OH$, or $CH_2(CH_2)_xOH$), or the standard is a compound with a structure wherein x is an integer between 1 and 12 (preferably between 1 and 6).

The positions on the phenanthrene moiety are numbered in the following manner:

Examples of standards usable in the present invention are:
phenanthrene-9-carboxaldehyde,
2-aminophenanthrene,
3-aminophenanthrene,
4-aminophenanthrene,
9-aminophenanthrene,
9,10-diaminophenanthrene,
3,4-dihydroxyphenanthrene,
1-hydroxyphenanthrene,
2-hydroxyphenanthrene,
2-nitrophenanthrene,
3-nitrophenanthrene,
9-nitrophenanthrene,
1-phenanthrene carboxylic acid,
2-phenanthrene carboxylic acid,
3-phenanthrene carboxylic acid,
3-phenanthronitrile,
9-phenanthrene carboxylic acid,
3-phenanthrene carboxylic acid,
2-phenanthrene sulfonic acid,
3-phenanthrene sulfonic acid,
9-phenanthrene sulfonic acid,
5 phenanthrene quinone,
gamma-oxo-2-phenanthrenebutyric acid,
9-cyanophenanthrene, and
4-phenanthrene methanol.

In a particular embodiment, step (3) of the immunoassay above comprises three steps, 3A, 3B, and 3C:

3A) quantitating the amount of the antibody preparation that reacted with the sample in step (1), 3B) quantitating the amount of the antibody preparation that reacted with the known amount of standard in step (2), and 3C) utilizing the amounts quantitated in steps (3A) and (3B) and the known amount in step (2) to calculate the amount or an upper or lower limit to the amount of analyte present in the sample used in step (1).

In a particular embodiment, the immunoassay of the invention comprises reacting an antibody preparation with the analyte, said antibody preparation prepared by using an immunogen that comprises both anthracene and chrysene linked to a carrier (preferably a protein) or carriers.

Preferably the analyte has a 50% B/Bo that is not more than four times the 50% B/Bo of phenanthrene and not less than one fifth the 50% B/Bo of phenanthrene.

Most preferably the analyte is selected from the group:
phenanthrene,
fluoranthene,
benzo[a]pyrene,
pyrene,
chrysene,
anthracene,
indeno[1,2,3-cd]pyrene,
1,2-benzoanthracene,
fluorene, and
benzo(b)fluoranthene.

The immunoassay is particularly useful when the analyte is part of a mixture selected from the group, creosote, diesel fuel, fuel oil (1, 2, 3, 4, 5, 6), coal tar and home heating oil.

In a preferred embodiment of the invention, the immunoassay is one wherein the standard is a substantially pure preparation of a single compound. However, the standard may, for example, be a mixture of one or more substantially pure compounds, said mixture constructed by mixing together portions of substantially pure preparation of said compounds.

A substantially pure preparation of a compound is one in which substantially all of the compounds have the same structure. A substantially pure preparation is therefore different from home heating oil or other mixtures of compounds.

The analyte is the compound being tested for.

The immunoassay of this invention is an assay for an analyte that may be one of several analytes detectable in the assay. The fact that the immunoassay can test for more than one analyte at the same time is because of the crossreactivity of the antibody used in the assay. In Example 2, below, a number of PAHs will be seen to have reactivity to the antibody used in the immunoassay. (Such cross-reactivity occurs in PAH immunoassays in general, not just the one exemplified herein.) Therefore, if the nature of the analyte in the sample is unknown, then for each possible analyte one can only assign an upper limit to the concentration of that analyte. Alternatively, for example, if the color (or other response) generated in a competitive immunoassay is greater than the amount generated by a standard then the assay provides a lower limit (that of the standard) to the amount of analyte. For many purposes, however, such information is sufficient to determine the extent and degree of contamination, to delineate pollutant plumes in ground water, to monitor well placement, and for preliminary identification and quantitation of pollutants.

A highly preferred standard is phenanthrene-9-carboxaldehyde, which is commercially available from Aldrich Chemical Company, Milwaukee, Wis. and Chem Service, West Chester, Pa.

The standards chosen for superior stability are ones expected to show both cross-reactivity with the antibody and good solubility in the co-solvents used to store them.

The immunoassays to which the present invention is applicable include: (1) Competition assays where the analyte competes with a detectable conjugate (e.g., as used in the Examples, an antibody-reactive moiety linked to an enzyme that can catalyze a reaction generating a colored compound) for binding sites provided by an antibody and detection is accomplished by measuring the decrease in the amount of detectable conjugate bound to the antibodies; (2) non-competition assays, where the analyte does not have to compete for such binding sites and the antibody is labelled with a detectable label; (3) sandwich assays, where one anti-analyte antibody acts as a bridge to bind the analyte to a solid phase, and detection is accomplished with a detectably-labelled second anti-analyte antibody that is allowed to attach the solid phase-bound analyte; or (4) any other immunoassay format. Indeed the term "immunoassay" is intended here in a very general sense and is any assay in which an antibody specific for an analyte of interest is used. Nevertheless, for the smallest analytes, sandwich assays may be difficult because of the need for two antibody binding sites.

The antibodies may be polyclonal or monoclonal. The use of hybridomas to create monoclonal antibodies is well known in the art. The fact that polyclonal antibodies against a compound can be created is an indicator that a monoclonal antibody against that compound can be created.

Detectable labels include enzymatic, fluorescent, radioactive, and chemiluminescent labels. The labels may be linked directly to other molecules of interest, such as antibodies, or indirectly by streptavidin-biotin linkages or other linkages. The labels may be bound directly to the antibodies or conjugates, or alternatively, be generated from substrates by enzymes attached to antibodies or substrates.

PREPARATION AND STRUCTURE OF THE IMMUNOGEN USED TO MAKE THE ANTIBODIES USED IN THE EXAMPLES

2-Succinamidoanthracene was synthesized as follows: 2-aminoanthracene was reacted with succinic anhydride in dioxane at 90° C. for 3 hours. On cooling to room temperature, the crystals formed were collected by suction filtration. The product was 2-succinamidoanthracene.

6-succinamidochrysene was synthesized as follows: 6-aminochrysene was reacted with succinic anhydride in dioxane-DMF (4:1) at 60°–70° C. for 4 hours. Water was then added and the solution allowed to stand at room temperature (about 20° C.) overnight. The solid obtained was collected by suction filtration. The product was 6-succinamidochrysene.

The ligand (0.6 mmole), either 2-succinamido anthracene or 6-succinamido chrysene in 10 mL of dry dimethylformamide ("DMF"), was treated with 2.4 mL of 0.25M triethylamine. The solution was cooled in ice-water, then 2.4 mL of 0.25M iso-butyl chloroformate was added and after 10 min the reaction solution was removed from the ice-water bath. After a total of 30 min of reaction time, the solution was added dropwise to a stirred and ice-cold solution of 300 mg carrier protein dissolved in 45 mL of 0.2M sodium borate, pH 8.7 and 30 mL of DMF. Cooling was maintained in an ice-water bath. The addition of the activated ligand required about 10 min. One hr after the complete addition, the solution was removed from the ice-water bath and stirred at room temperature another 2 hr. Dialysis was carried out against 0.1M sodium borate, pH 8.7, and then against two changes of water, all at 4° C. The product was freeze dried.

PREPARATION OF THE ANTIBODIES USED IN THE EXAMPLES

The immunogens were injected into rabbits and the antibodies were prepared as follows: The immunogen was dissolved or suspended in sterile saline to a concentration of 4 mg/ml. It was mixed with an equal amount of Freund's complete adjuvant and then emulsified. On Day 1, a total of 0.5 ml of the emulsion was injected into the hip muscle of the rabbit and a control bleed was done. On Day 20, the back of the animal was shaved and, in 6–8 sites, a total of 0.5 ml of emulsion was injected. On Day 30, a test bleed was done. On day 45, the immunization of Day 20 was repeated. On Day 55, a test bleed was done.

The immunization described for Day 20 is repeated at 30-day intervals using Freund's incomplete adjuvant. The interval is lengthened if antibody production was inadequate or the animal was distressed.

The animal was bled 7–10 days after immunization (30–50 ml). Bleeds were then screened for cross-reactivity to the various PAHs and selected bleeds from the anthracene and chrysene immunized rabbits were pooled to obtain a pool of rabbit anti-PAH antisera with broad specificity against PAHs.

PREPARATION OF THE ENZYME CONJUGATE USED IN THE EXAMPLES

The anthracene ligand, 2-succinamido anthracene (10 mg), was dissolved in 0.5 mL DMF and placed in an ice-bath. Tributylamine (80 μL), followed by isobutylchloroformate (40 μL) were added to the ligand solution. Stirring for 30 minutes at 8°–12° C. followed. The reaction mixture was then centrifuged to remove any precipitates. Added (124 μL) of the anhydride formed to 500 μL of a 3 mg/mL HRP (horse radish peroxidase) solution in carbonate buffer, pH 9.0, and stirred overnight at 4° C. The reaction mixture was then centrifuged and the supernatant purified through a Sephadex G-25 column using PBS, pH 5.0 (phosphate buffered saline, 25 mM phosphate, 150 mM sodium chloride, pH 5.0) as the mobile phase.

PREPARATION OF THE ANTIBODY-LINKED MAGNETIC PARTICLES

Attachment of the rabbit anti-PAH antibodies to magnetic particles was done as follows: One mL of a 50 mg/ml suspension of BioMag 4100 amine-terminated particles (Perseptive Diagnostic, Cambridge, Mass.) was activated with 5% (v/v) glutaraldehyde in 2 mL of 0.01M MES buffer, pH 6 (MES is 2-N-morpholine)ethanesulfonic Acid) for 3 hours. Unreacted glutaraldehyde was removed by washing four times with 5 ml of 0.01M MES buffer. Goat anti-rabbit IgG was diluted to an antibody concentration of 5 mg/mL and 1 mL was reacted with the activated magnetic particles by shaking for 16 hours. A 1M glycine solution was then used to quench any unreacted sites for 30 minutes. The particles were washed four times with 5 ml of Tris buffered saline with 0.1% bovine serum albumin (BSA), pH 7.4 and diluted in Tris buffered saline with 0.1% gelatin, pH 7.4 to achieve an iron concentration of 12–15 mg/ml. Rabbit anti-PAH antisera was then added at a 1:30,000 dilution and incubated for at least 30 minutes to allow coupling.

ASSAY PROCEDURE USED IN THE EXAMPLES

The sample to be tested was added, along with the enzyme conjugate, to a disposable test tube followed by the addition of paramagnetic particles with analyte-specific antibodies attached. At the end of an incubation period, a magnetic field was applied to hold the paramagnetic particles (with analyte and enzyme-conjugate bound to the antibodies on the particles, in proportion to their original concentration in the tube) in the tube and allow the unbound reagents to be decanted. After decanting, the particles were washed with Washing Solution.

The presence of analyte was detected by adding the enzyme substrate (hydrogen peroxide) and the chromogen (3,3'5,5'-tetramethylbenzidine). The enzyme-conjugate bound to the anti-analyte antibody catalyzes the conversion of the substrate/chromogen mixture to a colored product. After an incubation period, the reaction was stopped and stabilized by the addition of acid. Since the conjugate was in competition with the unlabeled analyte for the antibody sites, the color developed was inversely proportional to the concentration of analyte in the sample.

The anti-analyte antibody was a rabbit antibody covalently bound to paramagnetic particles, which were suspended in 150 mM Tris, 150 mM NaCl, 1 mM EDTA, 0.1% Gelatin, with 15 ppm active Proclin (manufactured by Rohm and Haas, purchased from Supelco), pH 7.4.

The enzyme-conjugate was in 25 mM sodium acetate, 150 mM NaCl, 4 mM DNS, 0.1 mM Luminol, 0.1% Gelatin with 15 ppm active Proclin, pH 5.0.

Each standard, calibrated to have an immunoreactivity equivalent to specific total phenanthrene concentrations, was in 25 mM sodium acetate, 150 mM NaCl, 0.1% Gelatin, with 15 ppm active Proclin containing 25% methanol, pH 5.0.

A solution containing 25% methanol can be made, for example, by adding 25 ml of methanol to 75 ml of an aqueous solution containing the other ingredients needed to make the desired final solution.

The Diluent/Zero Standard was 25 mM sodium acetate, 150 mM NaCl, 0.1% Gelatin, with 15 ppm active Proclin containing 25% methanol, pH 5.0 but without detectable analyte.

The Color Solution used in the Examples was obtained as a 3,3',5,5'-tetramethylbenzidine/peroxide system from Kirkegaard and Perry Laboratories (Gaithersburg, Md.).

The Stopping Solution was a solution of sulfuric acid (0.5%).

The Washing Solution was deionized water with 0.05% Triton X-100 with 15 ppm active Proclin.

Test tubes were polystyrene tubes.

Reagents were stored at 2°–8° C., not frozen.

A photometer was used to absorb the absorbance at 450 nm.

All reagents were allowed to come to room temperature and the antibody-coupled paramagnetic particles were mixed thoroughly just prior to pipetting into the assay.

Foam formation was avoided during vortexing.

The magnetic separation rack consisted of two parts: an upper rack which securely held the test tubes and a lower separator which contained the magnets used to attract the antibody-coupled paramagnetic particles. During incubations, the upper rack was removed from the lower separator so that the paramagnetic particles remained suspended during the incubation. For separation steps, the rack and the separator were combined to pull the paramagnetic particles to the sides of the tubes. The rack was decanted by inverting it away from the operator using a smooth turning action so that the liquid flowed consistently along only one side of the test tube. While still inverted, the rack was placed on an absorbent pad and allowed to drain. The rack was lifted replaced gently onto the pad several times to insure complete removal of the liquid from the rim of the tube.

The total time required for pipetting the magnetic particles was kept to two minutes or less.

The assay was done as follows:

1. 250 µl of either standard or control was added to each tube.

2. 250 µl of enzyme conjugate was added to each tube.

3. The antibody-coupled paramagnetic particles were mixed thoroughly and 500 ul of them were added to each tube (The stock solution was diluted to obtain a concentration of 12–15 mg iron/ml in 150 mM Tris, 150 mM NaCl, 1 mM EDTA, 0.1% Gelatin with 15 ppm Proclin, pH 7.4, and 500 ul was added to each tube).

4. Tubes were vortexed for 1 to 2 seconds minimizing foaming.

5. Tubes were incubated for 30 min at room temperature (15°–30° C.).

6. Tubes in the magnetic rack were placed over a magnetic base for two minutes.

7. The tubes were decanted and gently blotted briefly in a consistent manner.

8. One ml of Washing Solution was added to each tube, the tubes are vortexed for 1–2 seconds, and the tubes were allowed to remain in the separation rack for two minutes.

9. The tubes were decanted and gently blotted briefly in a consistent manner.

10. Steps 8 and 9 were repeated an additional time.

11. The rack was removed from the separator and 500 µl of Color Solution was added to each tube.

12. Vortexing was done for 1 to 2 seconds minimizing foaming.

13. Incubation was done for 20 minutes at room temperature.

14. 500 µl of Stopping Solution was added to each tube.

15. The results were read at 450 nm within 15 minutes after adding the Stopping Solution.

It is recommended that, in general, precision pipets capable of delivering 250 ul and 500 µl, and a 1.0 ml repeating pipet be used; that reagents are added directly to the bottom of the tube while avoiding contact between the reagents and the pipet tip; that clean pipets be used for each sample; and that contact between reagent droplets on the tubes and pipet tips be avoided. To minimize loss of volatile compounds, the sample, conjugate and particle addition steps are performed in as timely a fashion as possible.

A Thermolyne Maxi Mix, Scientific Industries Vortex Genie, or equivalent vortex mixer may be used.

Data can, if desired, be analyzed by a commercially available data storer and analyzer, such as the Ohmicron RPA-I Analyzer available from Ohmicron, Newtown, Pa. 18940. Such automated analyzers are used to make direct optical readings and use a microprocessor to convert optical readings to sample concentrations by comparing the results to those obtained with calibration curves.

USE OF THE ASSAY IN THE FIELD

For use in the field, the sample to be tested for analyte concentration is water or diluted soil extract. Water samples are collected in glass containers with Teflon caps and diluted 3:1 with methanol (3 parts water and 1 part methanol). Soil samples may be analyzed by extracting them with calcium chloride in 100% methanol and then diluting them 1:50 in Diluent.

Samples containing gross particulate matter are filtered (e.g., with 0.2 µm Anotop® 25 Plus, Whatman, Inc.) to remove particles.

If the analyte concentration of a sample exceeds 50 ppb of phenanthrene or its immunoreactive equivalent, the sample is subject to repeat testing using a diluted sample. Prior to assay, a ten-fold or greater dilution of the sample is recommended with an appropriate amount of Diluent/Zero Standard and mixing thoroughly.

Although not used in the Examples, a Control sample is recommended for routine use of the immunoassay. The Control, calibrated to have an immunoreactivity equivalent to a concentration of approximately 25 ppb phenanthrene, is in 25 mM acetate, 150 mM NaCl, 0.1% Gelatin, 25% methanol, with 15 ppm active Proclin, pH 5.0. The Control sample can be used to determine whether the assay is providing the correct value for analyte concentration.

A standard curve is constructed by plotting the % $B/B_o$ for each standard on vertical logit (Y) axis versus the corresponding analyte concentration on a horizontal algorithmic (X) axis. The % $B/B_o$ for controls and sample will then yield levels in ppb of analyte by interpolation using the standard curve.

EXAMPLES

Example 1

Study of Standard Stability

Standards were prepared by weighing 100 +/−1 mg of phenanthrene and dissolving it in 10.0 mL of DMF (dimethylformamide). This 10 mg/mL solution was diluted 1.0 mL into 100 mL methanol for a 100 µg/ml solution. The 100 µg/mL solution was then diluted 1.0 mL into 100 mL of Diluent (25 mM sodium acetate, 150 mM NaCl, 0.1% Gelatin, 25% methanol, 15 ppm Proclin) to provide a 1 µg/mL solution. Standards were prepared from the 1 µg/mL solution volumetrically at 2, 10, and 50 ppb by dilution with diluent.

Phenanthrene has a 50% B/Bo of 16.5 ppb and phenanthrene-9-carboxaldehyde has a 50% B/Bo of 13.0 ppb. Phenanthrene-9-carboxaldehyde solutions were prepared by first preparing a 10 mg/mL solution of that compound in DMF. This 10 mg/mL solution was then diluted 1.0 mL into 100 mL methanol for a 100 µg/mL solution. The 100 µg/mL solution was then diluted 1.0 mL into 100 mL of diluent to provide a 1 µg/ml solution from which standards were prepared at 1, 7.5 and 50 ppb of phenanthrene-9-carboxaldehyde by dilution with Diluent.

Stability studies were conducted by aliquoting prepared standards (0, 2, 10 and 50 ppb for phenanthrene and 0, 1, 7.5 and 50 ppb for phenanthrene-9-carboxaldehyde) into 5 mL glass vials at a volume of 2.5 mL. The vials were then capped with Teflon coated caps and crimped. The vials were then separated into five groups. Each group was then placed at a different temperature (−20° C., 2°–8° C., 20°–25° C., 37° C. and 50° C.) in an upright position. Standards were tested for B/Bo at specified intervals by assaying each standard level in duplicate for each temperature. The results were then graphed as a function of time (x) versus B/Bo(y) by temperature level. (See FIGS. 1–5) (B/Bo is the absorbance at 450 nm observed for phenanthrene or phenanthrene-9-carboxaldehye at the specified concentration divided by the absorbance using diluent/zero standard instead of either phenanthrene or phenanthrene-9-carboxaldehyde.)

The results show that the B/Bo of phenanthrene-9-carboxaldehyde shows less change as a function of time of storage than the B/Bo of phenanthrene does. The superior stability of the phenanthrene-9-carboxaldehyde solutions becomes more marked as the temperature of storage is increased.

Figure 1:
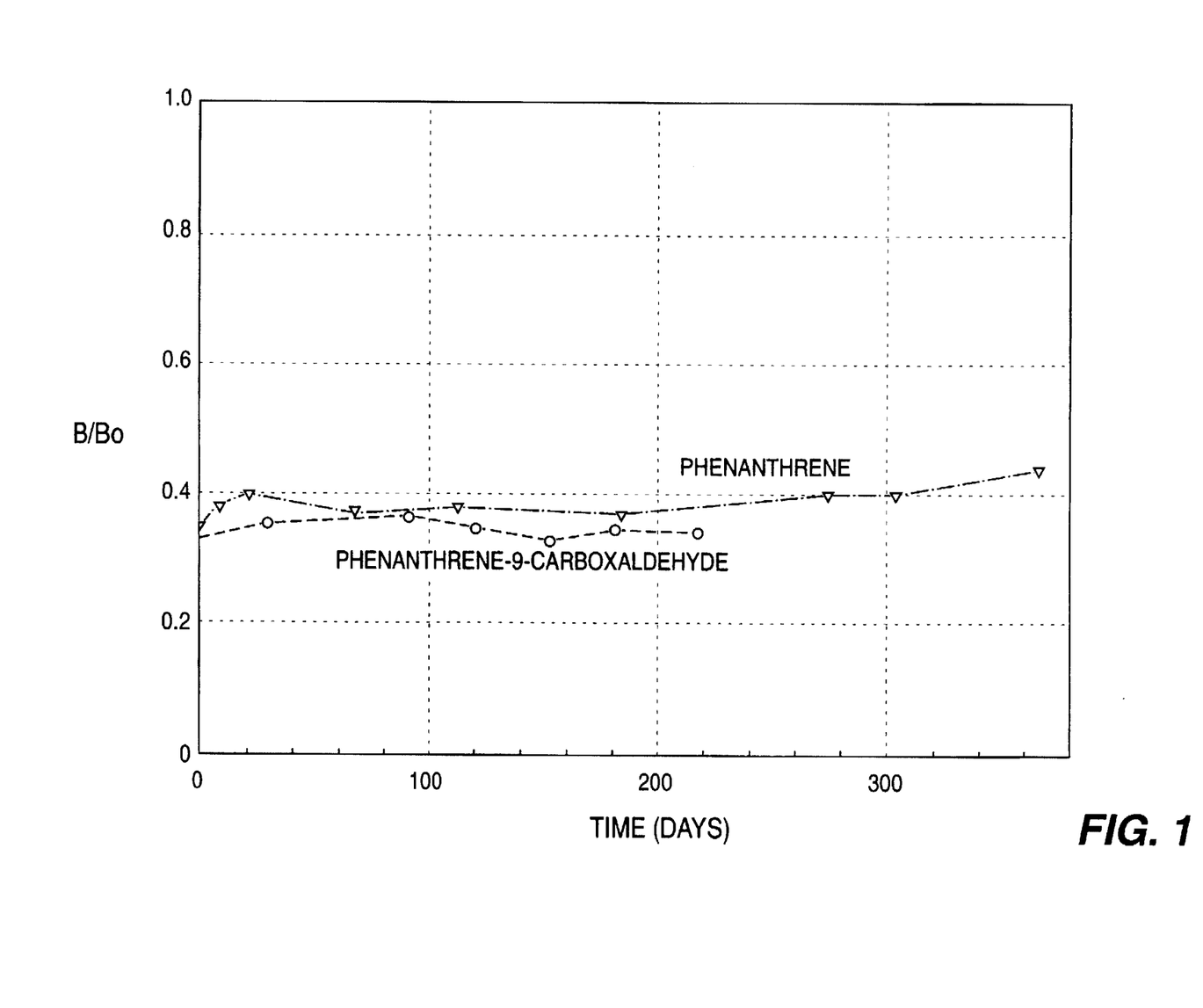
FIG. 1. B/Bo's of phenanthrene and phenanthrene-9-carboxaldehyde as a function of their time of storage at −20° C.
Figure 2:
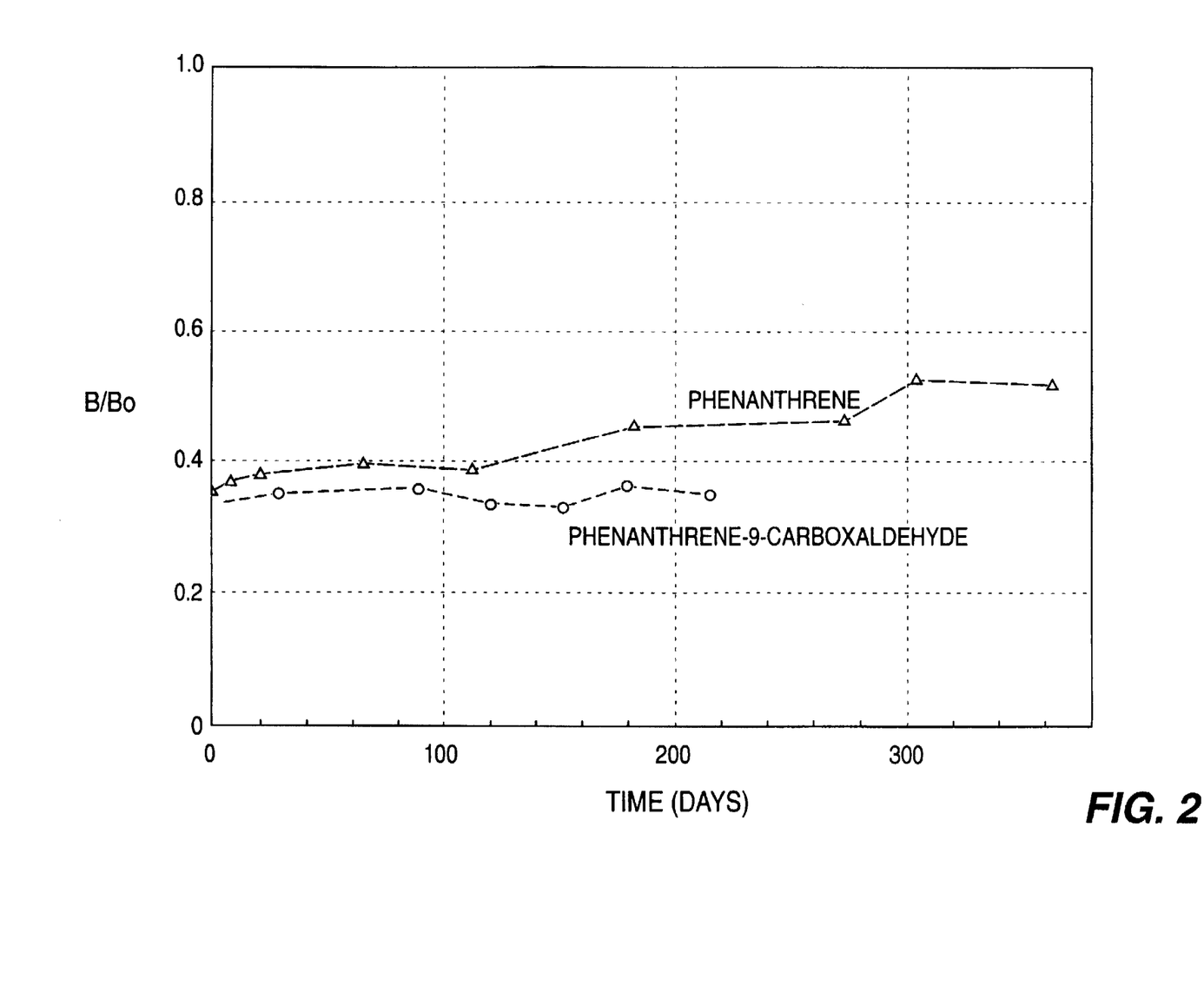
FIG. 2. B/Bo's of phenanthrene and phenanthrene-9-carboxaldehyde as a function of their time of storage at 4° C.
Figure 3:
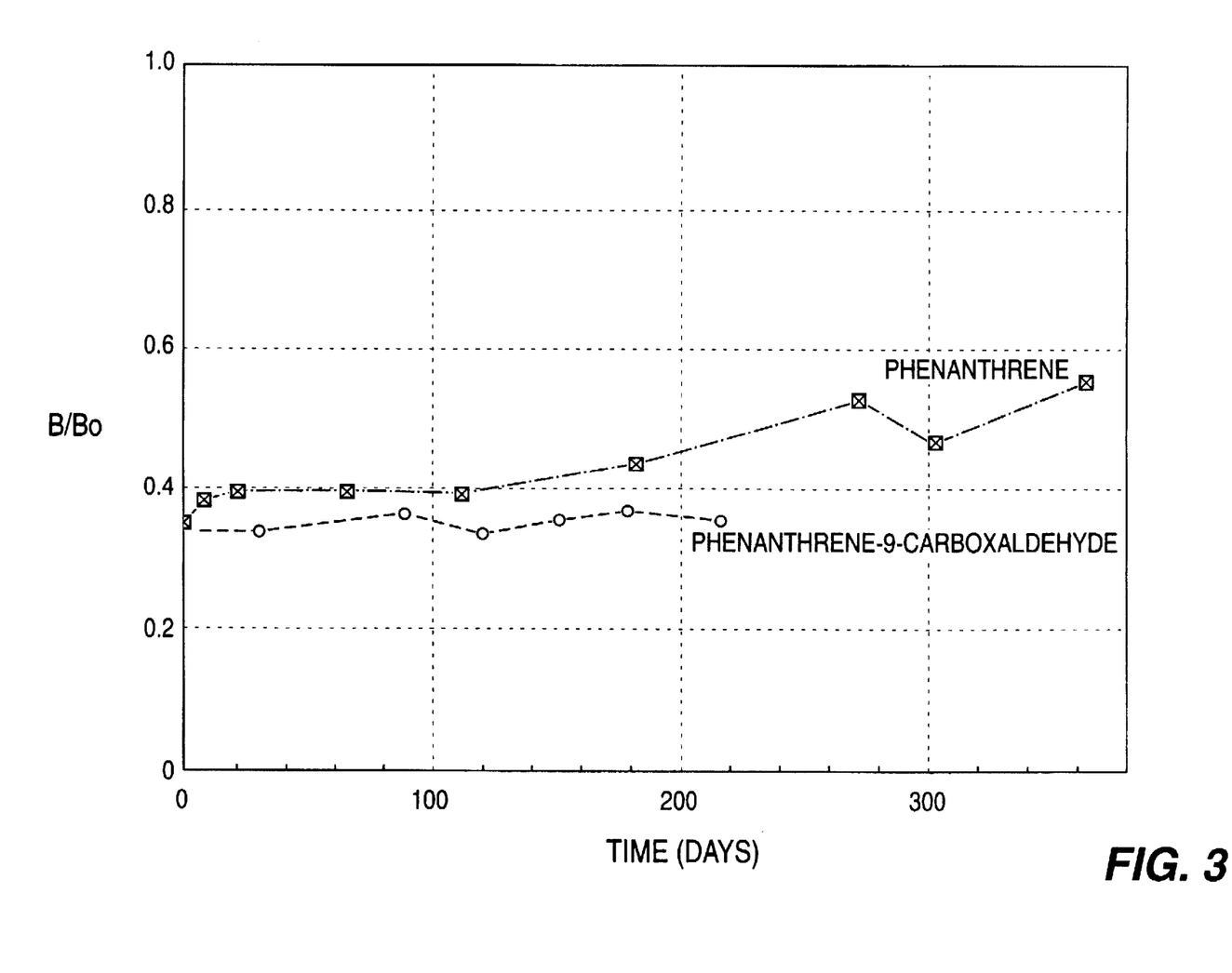
FIG. 3. B/Bo's of phenanthrene and phenanthrene-9-carboxaldehyde as a function of their time of storage at room temperature (about 20°–25° C.).
Figure 4:
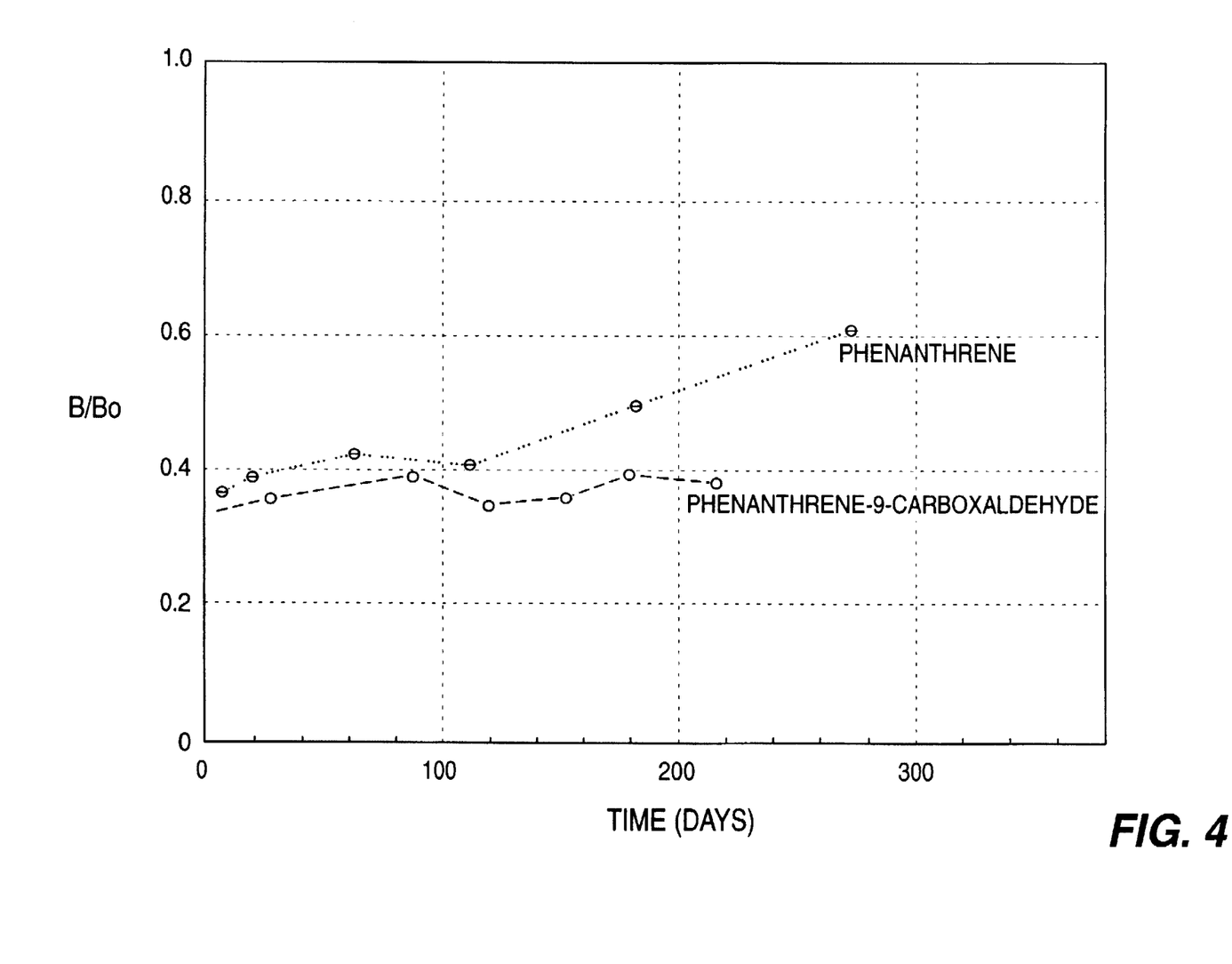
FIG. 4. B/Bo's of phenanthrene and phenanthrene-9-carboxaldehyde as a function of their time of storage at 37° C.
Figure 5:
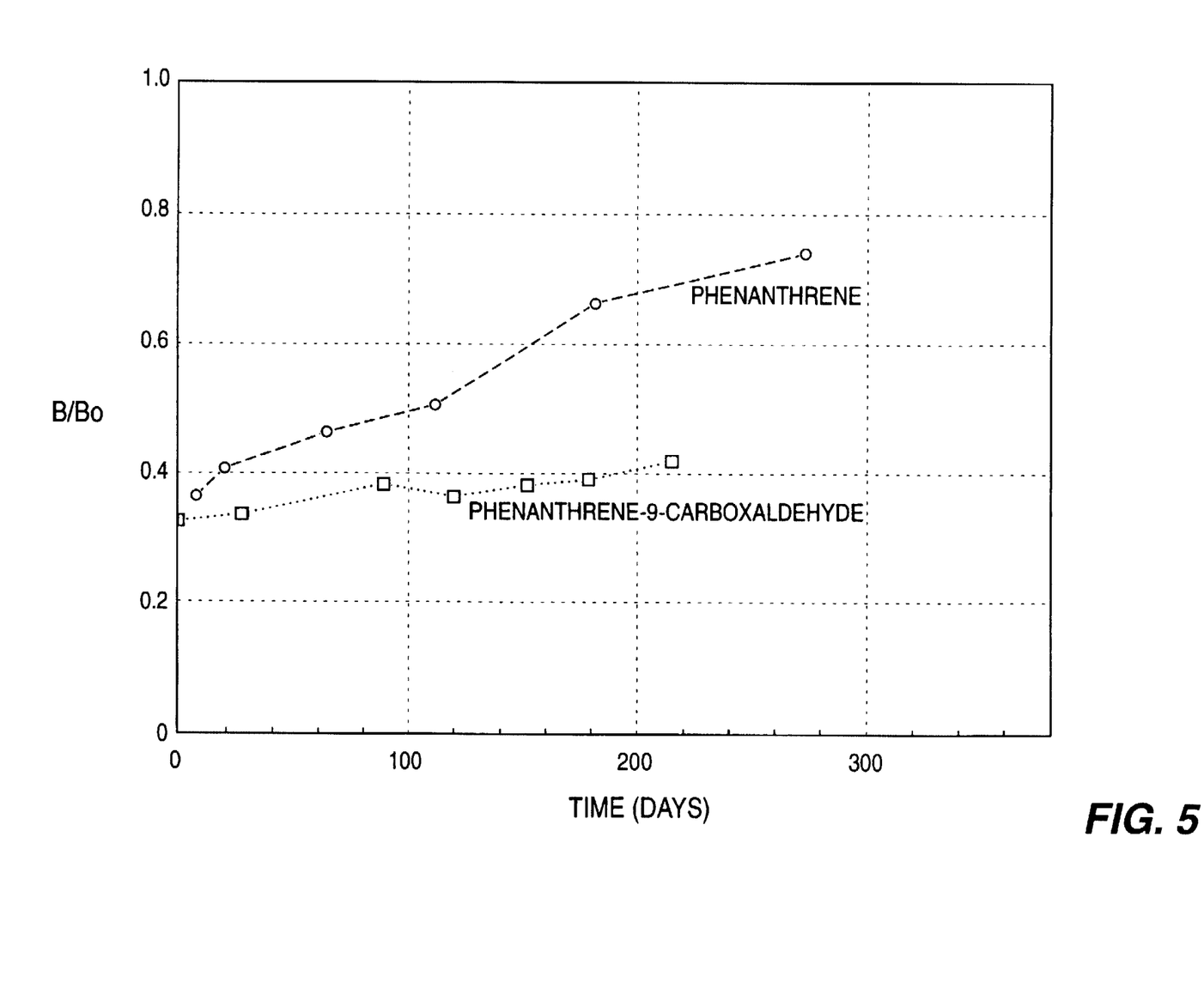
FIG. 5. B/Bo's of phenanthrene and phenanthrene-9-carboxaldehyde as a function of their time of storage at 50° C.

In FIG. 2, for example, there was an apparent 25 percent increase in the B/Bo of the phenanthrene after 200 days of storage at 4° C. Because, as illustrated in Example 3, there is not a linear relationship between B/Bo and concentration of a standard (or analyte), a 25% error in B/Bo will result in considerably more than a 25% error in the analyte concentration determined by the immunoassay.

Example 2

Cross-reactivity Studies

The cross-reactivity, of the antibodies used in the assay, for various hydrocarbons was tested and the results expressed both as 50% B/Bo and as least detectable dose (LDD) which is estimated as the dose needed to generate a $B/B_o$ of 90%. (If the mean absorbance value for the standard is 0.5 times the mean absorbance value for the Diluent/Zero Standard then the % $B/B_o$ is 50% and the concentration of standard used is the 50% $B/B_o$ concentration. A B/Bo of 90% means B equals 0.9 times $B_o$). The results are tabulated in Table 1:

TABLE 1

| Cross-reactivity Studies | | |
|---|---|---|
| compound | LDD (ppb) | 50% B/Bo (ppb) |
| phenanthrene | 0.70 | 16.5 |
| fluoranthene | 0.32 | 4.7 |
| benzo(a)pyrene | 0.50 | 6.9 |
| pyrene | 0.20 | 7.7 |
| chrysene | 0.40 | 7.8 |
| anthracene | 0.54 | 11.0 |
| indeno(1,2,3-c,d)pyrene | 0.78 | 27.2 |
| 1,2 benzoanthracene | 0.77 | 28.4 |
| fluorene | 1.65 | 35.2 |
| benzo(b)fluoranthene | 0.91 | 54.2 |
| benzo(k)fluoranthene | 0.77 | 524 |

Example 3

Calculation of 50% $B/B_o$

Figure 6:
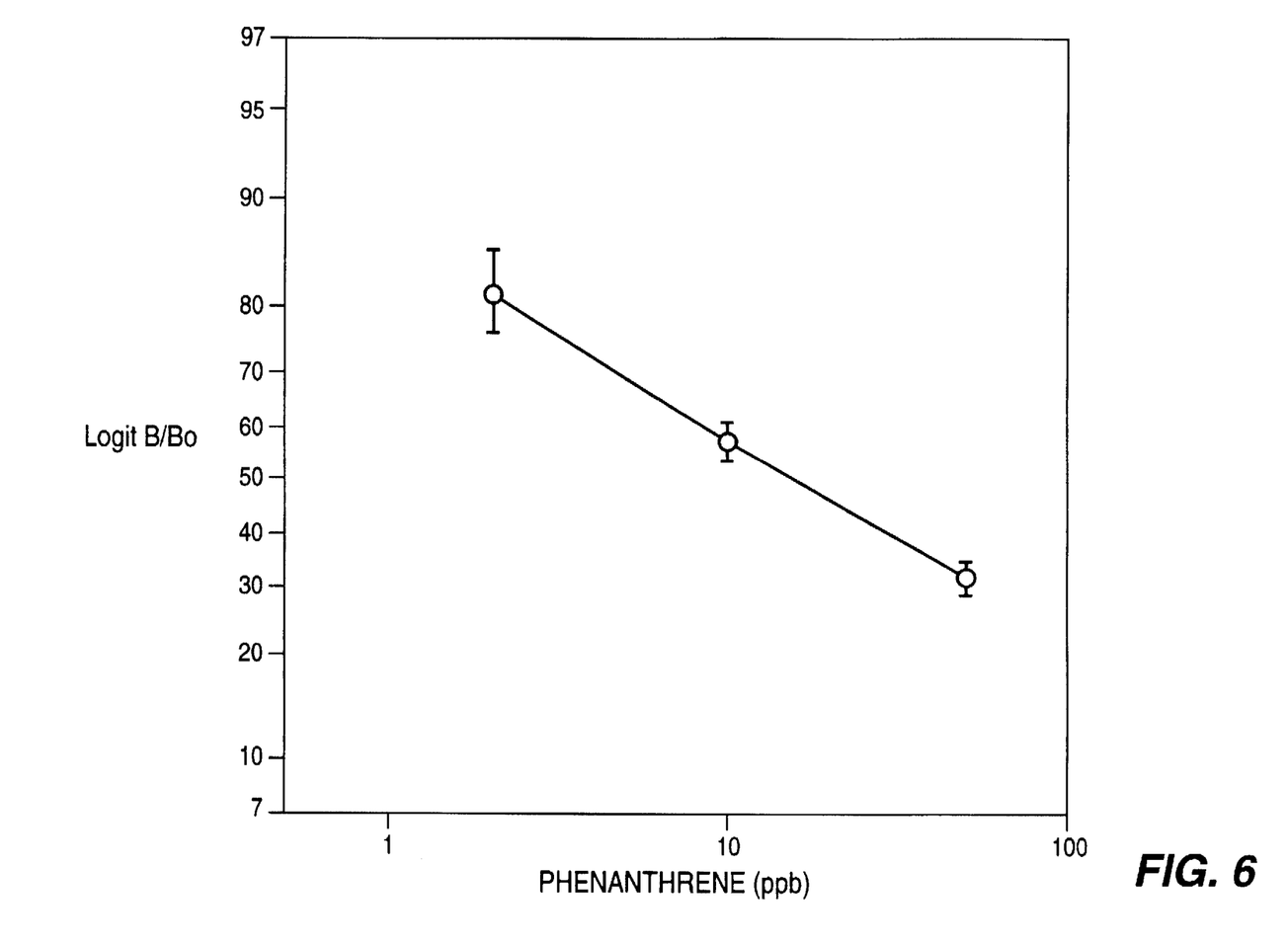
FIG. 6. B/Bo of phenanthrene as a function of its concentration.

An example of a curve plotting the % $B/B_o$ for a standard on vertical logit (Y) axis versus the corresponding analyte concentration on a horizontal algorithmic (X) axis is shown in FIG. 6. The curve is for phenanthrene. The value for 50% $B/B_o$ is 16.5 ppb.

Example 4

Four environmental water sources (two ground waters and two municipal waters) were each spiked with four different amounts of phenanthrene then, using phenanthrene-9-carboxaldehyde as a standard, each sample was analyzed with the immunoassay for phenanthrene as if the phenanthrene concentration was unknown. For each amount of spiked phenanthrene, the Mean of the phenanthrene value obtained with the immunoassay for the four samples was calculated, as was the standard deviation (S.D.) and the % recovery. The results are shown in Table 2.

TABLE 2

| | Recovery Studies | | |
|---|---|---|---|
| Phenanthrene Added (ppb) | Mean (ppb) | S.D. (ppb) | % Recovery |
| +5.0 | 5.09 | 0.58 | 102 |
| +7.5 | 8.13 | 0.56 | 108 |
| +20.0 | 21.46 | 2.47 | 107 |
| +40.0 | 40.91 | 2.99 | 102 |

What is claimed is:

1. An immunoassay for an analyte, said immunoassay a process that comprises the steps of:

1) reacting a sample with an antibody preparation, said sample comprising an unknown amount of analyte, said antibody reactive against said analyte, 2) reacting a known amount of standard with an antibody preparation of the same specificity as that used in step (1), it being required that the standard is a compound that is immunoreactive with the antibody preparation,

3) quantitating the amount of the antibody preparation that reacted with the sample in step (1), 4) quantitating the amount of the antibody preparation that reacted with the known amount of standard in step (2), and 5) utilizing the amount quantitated in steps (3) and (4) and the known amount in step (2) to calculate the amount or an upper or lower limit to the amount of analyte present in the sample used in step (1), wherein the analyte is selected from the group phenanthrene, fluoranthene, benzo[a]pyrene, pyrene, chrysene, anthracene, indeno[1,2,3-cd]pyrene, 1,2-benzoanthracene, fluorene, and benzo(b)fluoranthene, wherein either the standard is a compound with the structure wherein $R_1$, $R_2$, $R_3$, $R_4$, $R_5$, $R_6$, $R_7$, $R_8$, $R_9$, and $R_{10}$ are substituents, wherein one or two of said substituents is not H and the other substituents are H, and a substituent that is not H is either OH, COH, $CH_2OH$, $CH_2(CH_2)_xOH$, $CO_2H$, $NH_2$, CN, $SO_3H$, $NO_2$, or or the standard is a compound with a structure or wherein x is an integer between 1 and 12.

2. An immunoassay of claim 1 which comprises reacting an antibody preparation with the analyte, said preparation comprising antibodies prepared by using an immunogen selected from the group, anthracene linked to a protein and chrysene linked to a protein.

3. An immunoassay of claim 1 wherein the standard is a substantially pure preparation of a single compound.

4. A process of claim 1 wherein the standard is a mixture of one or more substantially pure compounds, said mixture constructed by first creating and then mixing together portions of pure preparation of said compounds.

5. A process of claim 1 wherein the standard is a compound with the structure wherein $R_1$, $R_2$, $R_3$, $R_4$, $R_5$, $R_6$, $R_7$, $R_8$, $R_9$, and $R_{10}$ are substituents, wherein one or two of said substituents are not H (i.e., not hydrogen) and the other substituents are H, and a substituent that is not H is either OH, COH, $CH_2OH$, $CH_2(CH_2)_xOH$, $CO_2H$, $NH_2$, CN, $SO_3H$, $NO_2$, or wherein x is an integer between 1 and 12.

6. A process of claim 5 wherein a substituent that is not H is either OH, COH, $CH_2OH$, or $CH_2(CH_2)_xOH$ and wherein x is an integer between 1 and 6.

7. A process of claim 5 wherein $R_1$, $R_2$, $R_3$, $R_4$, $R_5$, $R_6$, $R_7$, $R_8$, $R_9$, and $R_{10}$ are substituents, and wherein one of said substituents is not H and the other substituents are H.

8. A process of claim 5 wherein the standard is phenanthrene-9-carboxaldehyde.

9. A process of claim 1 wherein the standard is a compound with a structure or

10. A kit for performing the immunoassay of claim 1, said kit comprising the standard, an analyte-reactive antibody, and instructions for performing the immunoassay.

11. An immunoassay of claim 2 wherein the antibody preparation comprises both antibodies prepared by using an immunogen that is anthracene linked to a protein and antibodies prepared by using an immunogen that is chrysene linked to a protein.

* * * * *